US011738323B2

(12) United States Patent
Bitterwolf et al.

(10) Patent No.: US 11,738,323 B2
(45) Date of Patent: Aug. 29, 2023

(54) METHOD FOR PURIFICATION OF LIQUID COMPOSITIONS CONTAINING AT LEAST ONE SPHINGOLIPID

(71) Applicant: Clariant Produkte (Deutschland) GmbH, Frankfurt am Main (DE)

(72) Inventors: Carina Bitterwolf, Munich (DE); Joern Kretzschmar, Planegg (DE); Lina Tubes, Pentenried (DE); Benjamin Fuerst, Penzberg (DE)

(73) Assignee: Clariant Produkte (Deutschland) GmbH, Frankfurt am Main (DE)

( * ) Notice: Subject to any disclaimer, the term of this patent is extended or adjusted under 35 U.S.C. 154(b) by 0 days.

(21) Appl. No.: 17/642,477

(22) PCT Filed: Sep. 9, 2020

(86) PCT No.: PCT/EP2020/075129
§ 371 (c)(1),
(2) Date: Mar. 11, 2022

(87) PCT Pub. No.: WO2021/048160
PCT Pub. Date: Mar. 18, 2021

(65) Prior Publication Data
US 2023/0132025 A1      Apr. 27, 2023

(30) Foreign Application Priority Data
Sep. 11, 2019 (EP) .................................... 19196800

(51) Int. Cl.
*B01J 20/12* (2006.01)
*C07C 213/10* (2006.01)
*B01J 20/28* (2006.01)
*B01D 15/02* (2006.01)
*B01D 61/14* (2006.01)

(52) U.S. Cl.
CPC .............. *B01J 20/12* (2013.01); *B01D 15/02* (2013.01); *B01D 61/145* (2013.01); *B01J 20/28059* (2013.01); *B01J 20/28061* (2013.01); *B01J 20/28085* (2013.01); *C07C 213/10* (2013.01); *B01D 2311/2626* (2013.01)

(58) Field of Classification Search
None
See application file for complete search history.

(56) References Cited

FOREIGN PATENT DOCUMENTS

| EP | 1920829 A1 | 5/2008 |
|---|---|---|
| EP | 1893329 B1 | 8/2011 |
| EP | 2099561 B1 | 11/2013 |
| EP | 3110543 B1 | 12/2017 |
| WO | 2006131136 A1 | 12/2006 |

OTHER PUBLICATIONS

Anderson G. et al., "The Adsorption of Inositol Phosphates and Glycerophosphate by Soil Clays, Clay Minerals, and Hydrated Sesquioxides in Acid Media", Journal of Soil Sciences, vol. 13, No. 2, 1962, pp. 216-224.
Dickson R.C. et al., "Yeast sphingolipids", Biochimica et Biophysica Acta (BBA), vol. 1426, Issue 2, Jan. 6, 1999, pp. 347-357.

*Primary Examiner* — Sudhakar Katakam
*Assistant Examiner* — Jennifer C Sawyer
(74) *Attorney, Agent, or Firm* — Verrill Dana, LLP

(57) ABSTRACT

The present invention relates to a method for purification of liquid compositions containing at least one sphingolipid and the use of a specific clay mineral for the purification of such liquid compositions.

14 Claims, 8 Drawing Sheets

METHOD FOR PURIFICATION OF LIQUID COMPOSITIONS CONTAINING AT LEAST ONE SPHINGOLIPID

CROSS-REFERENCE TO RELATED APPLICATIONS

This application is the U.S. national phase of PCT/EP2020/075129, filed 9 Sep. 2020, which claims priority to European Appl. No. EP19196800.7, filed 11 Sep. 2019.

BACKGROUND

Since recent years chemical compounds produced from renewable resources are considered to be of high importance for sustainable production of a variety of consumer goods such as bioplastic, laundry, cosmetic, food or feed products, and it is expected that the demand will even further increase.

However, production of such compounds has been proven challenging. Most promising approaches relate to fermentative production using either natural or genetically modified microorganisms. Key challenges in this respect include to guarantee an industrial feasible process concerning yield and purity of the so-produced compounds. This applies in particular to microorganisms belonging to the kingdom of fungi such as yeasts and molds. Even though these microorganisms can be used as reliable producers of a huge variety of compounds, their tendency to also produce a wide range of by-products renders economical production difficult as many later applications require prior removal of these substances. A major obstacle is the formation of undesired by-products belonging to a group of compounds known as sphingolipids which lead to discoloration and formation of flocs, which often build up a firm sediment and/or cause turbidity of the product. This applies in particular when the fermentation medium has been sterilized prior to the fermentation process which is, however, obligatory for most commercial relevant production processes. Discoloration is a major problem in case the fermented product is to be used within bioplastic or food production, sediment formation will diminish effectiveness of further processing or require additional cost-intensive process steps.

SUMMARY

The present invention relates to a method for purification of liquid compositions containing at least one sphingolipid and the use of a specific clay mineral for the purification of such liquid compositions.

The inventors of the present invention have set themselves the task to provide a process for purification of liquid compositions containing at least one sphingolipid which is economically feasible but also environmentally friendly.

DETAILED DESCRIPTION

Figure 1:
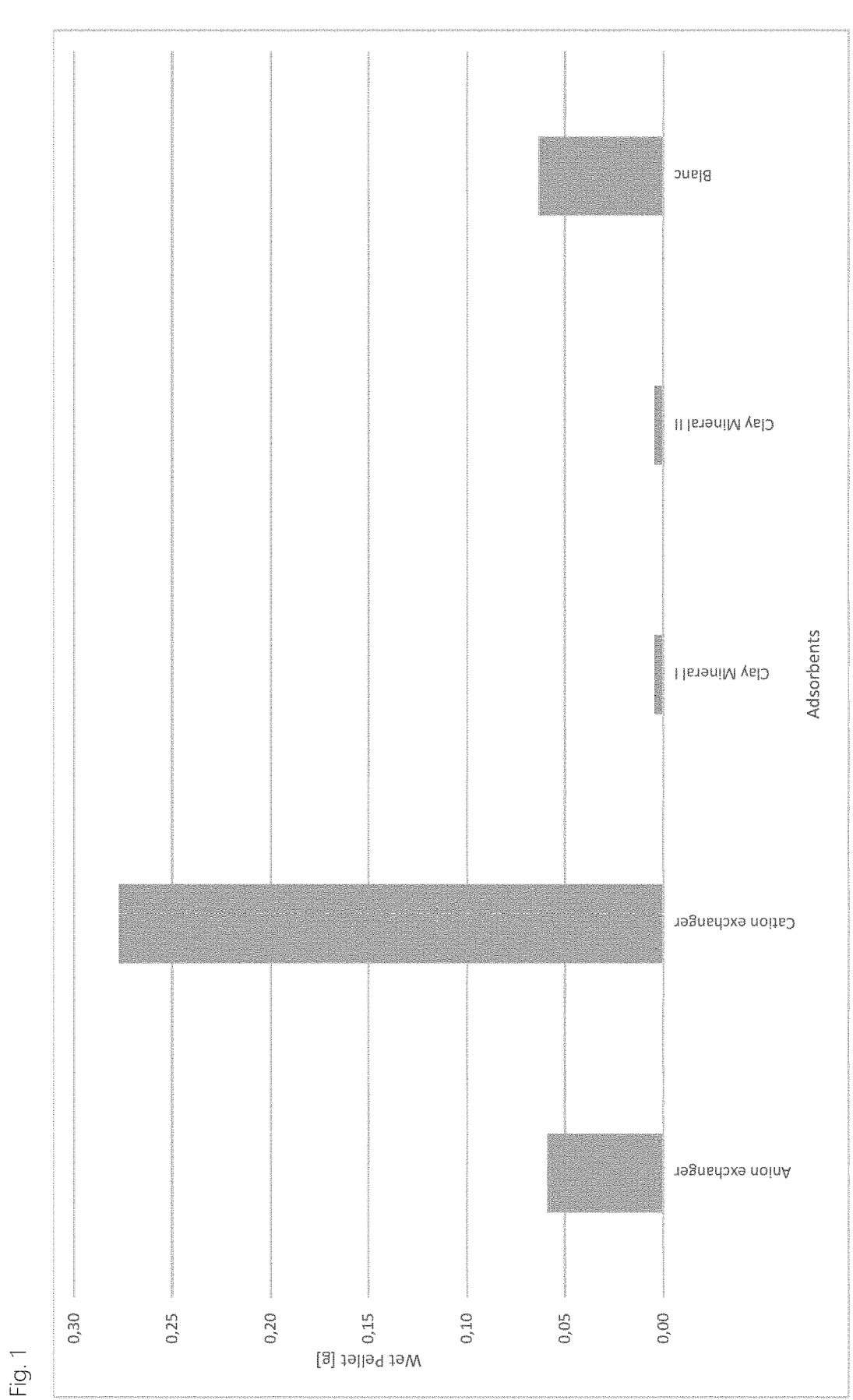
FIG. 1: shows the weight of sediment built up in an experiment, comparing several adsorbents regarding their performance in sediment prevention. Less pellet means better adsorbing performance. This figure illustrates example 1.
Figure 2:
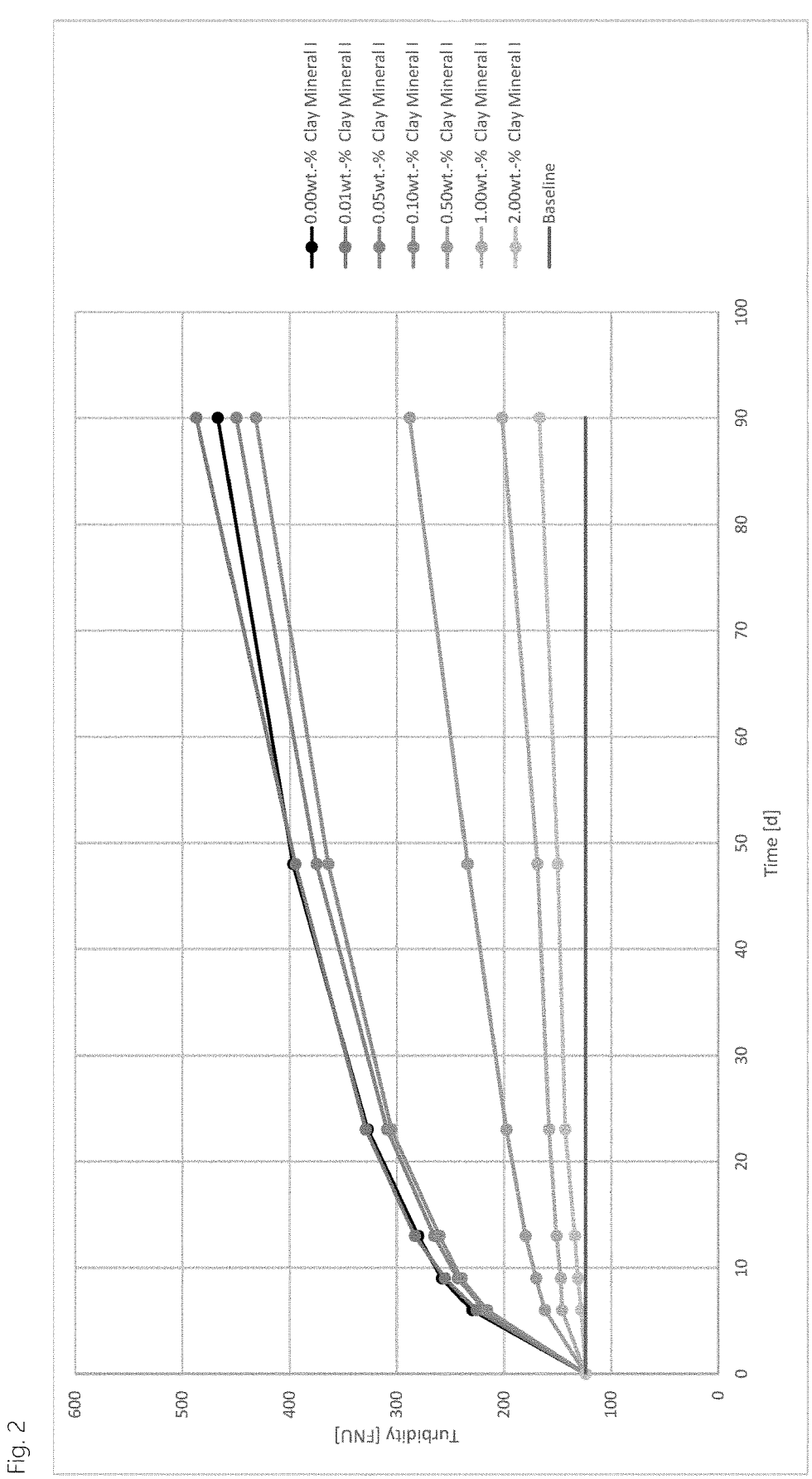
FIG. 2: shows the turbidity of filtrates after the treatment with several dosages of Clay Mineral I directly after the treatment and up to 90 days after. This figure illustrates example 2.
Figure 3:
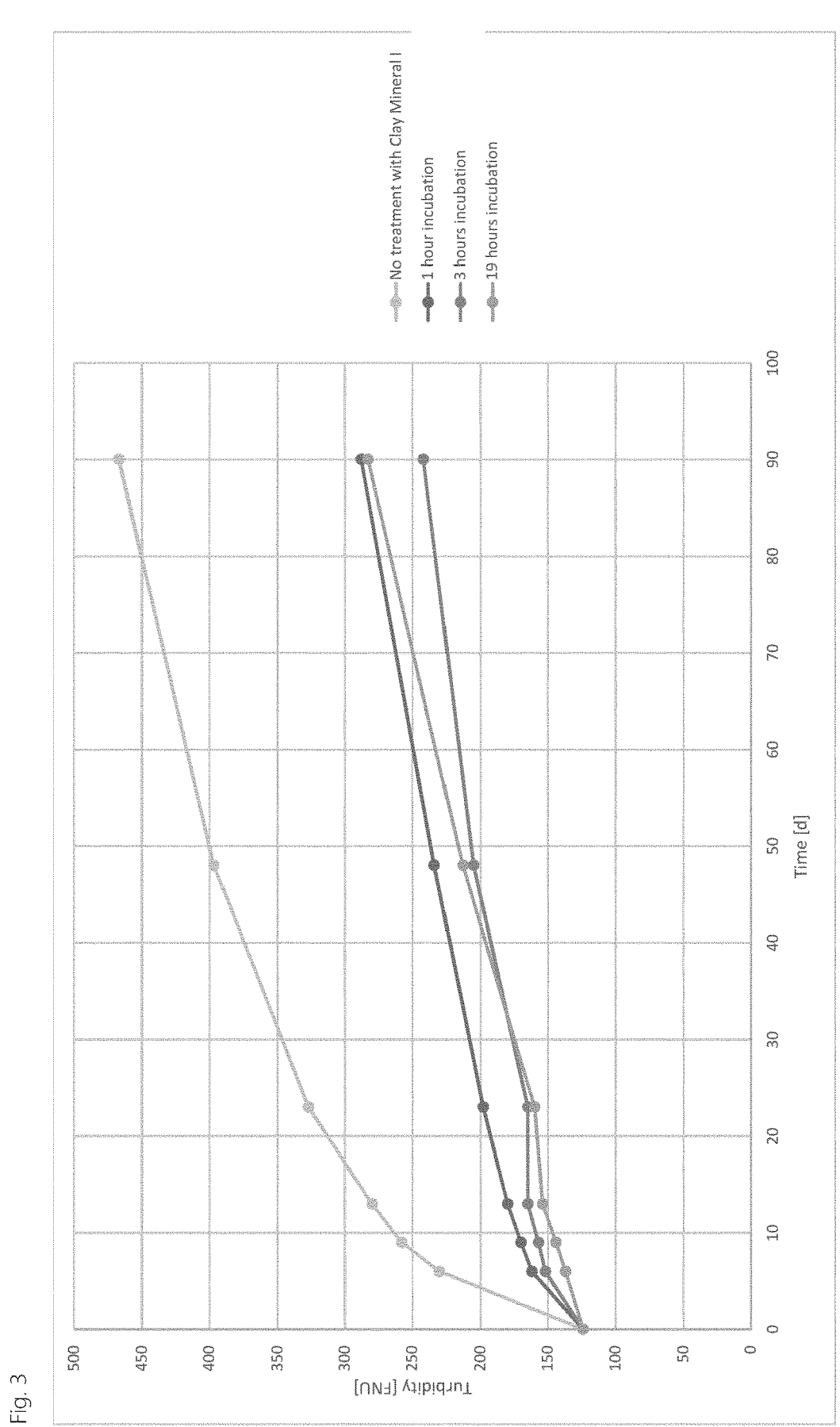
FIG. 3: shows the turbidity of filtrates after the treatment with Clay Mineral I directly after the treatment and up to 90 days after. In this experiment, the incubation time of the Clay mineral I treatment was varied. This figure illustrates example 3.

The present invention provides a method for purification of liquid compositions containing at least one sphingolipid comprising the following steps
 (a) adding from 0.1 to 35 wt.-% of a clay mineral with a BET surface area of from 50 to 450 m$^2$/g, a micropore volume of pores with a maximum diameter of 80 nm of from 0.01 to 0.75 ml/g, a SiO$_2$ content of from 25 to 98 wt.-% and a cation exchange capacity of from 20 to 120 mVal/100 g to the liquid composition;
 (b) separating the clay mineral after a reaction time of from 10 seconds to 90 minutes.

It has thereby surprisingly been found that the inventive process is not only suitable for industrial scale production as it does not show the disadvantages described above but will also enable the use of the so-removed sphingolipids for other applications by desorption. As both compounds are of high value for a variety of other industrial applications such as the production of cosmetic products this will contribute to the economical benefit of the inventive process. Even if further usage of these compounds is undesired the so-removed compounds can still be environmentally friendly disposed within biogas production processes. A further advantage of the inventive method is the long-term stability of the purified product even at higher temperatures. If the liquid composition is a fermented medium containing enzymes, the inventive process could not only keep turbidity values low during long time storage even at elevated temperatures but at the same time enzymatic activity of the enzymes could be maintained.

Within the present invention the term "liquid composition" is to be understood to refer to any composition in liquid form which contains at least one sphingolipid, whereas suitable liquid compositions contain at least 0.1 wt.-% of sphingolipids. Within a suitable embodiment of the inventive method, the liquid composition is a fermented medium wherein the inventive method is particularly suitable for a medium fermented by a microorganism belonging to the kingdom of fungi such as filamentous fungi or yeasts. Within the present invention, the term "fermented medium" refers to both, compositions still containing the microorganism (also referred to as "whole broth") or to compositions from which the microorganism has been removed (also referred to as "supernatant"). Particularly suitable are media with a high initial (i.e. prior to fermentation) content of glucose, such as a glucose content of from 20 to 85 wt.-% (weight glucose to weight water), from 30 to 85 wt.-%, from 40 to 85 wt.-t or from 45 to 80 wt.-%. Other particularly suitable medium further contain a certain amount of di- and/or oligosaccharides such as from 1 to 20 wt.-% (weight di- and/or oligosaccharide to weight water) or from 3 to 15 wt.-%. Within a further particularly suitable embodiment of the inventive method, the liquid composition is a fermented medium which has been heat-treated prior to fermentation, for example the medium may have been autoclaved before the fermentation took place. An autoclavation is carried out by subjecting the medium to elevated temperature and a pressure different from ambient air pressure. Autoclavation may take place at a temperature of from 100 to 140° C. for a time period of from 5 minutes to 12 hours or for a time period of from 30 minutes to 10 hours or from 1 hour to 10 hours. The method of autoclavation is well known to a person skilled in the art.

Within a particular suitable embodiment of the inventive method, the fermented medium is a medium fermented by a filamentous fungus. The filamentous fungus may be selected from the group consisting of *Acremonium, Aspergillus, Fusarium, Humicola, Mucor, Myceliophthora, Neurospora, Penicillium, Scytalidium, Thielavia, Tolypocladium* and *Trichoderma*. The fermented medium may also contain one or more enzymes. In case the fermented medium is a medium fermented by a filamentous fungus, the fermented medium contains at least one enzyme with hydrolytic activity such as but not limited to cellulases and hemicellulases, for example glucanases, xylanases, glucosidases, arabinofuranosidases or mannanases.

Within a particularly suitable embodiment of the inventive method, the liquid medium contains from 0.1 to 35 wt.-% of sphingolipids, wherein a content of from 0.5 to 25 wt.-%, from 1 to 20 wt.-% or from 5 to 15 wt.-% is also suitable for the inventive method.

Within the present invention the term "sphingolipid" refers to any kind of aliphatic amino alcohol. Within the present invention, the term "sphingolipid" comprises sphingoid bases and derivatives thereof. Examples are sphingosines, dihydrosphingosines, phytosphingosines, ceramides, sphingomyelins, glycosphingolipids and gangliosides.

Within the present invention, the term "sediment" refers to any substance comprising the at least one sphingolipid, at least one protein and at least one inorganic compound. It is built up during storage of the liquid composition and originates from flocs which sediment on the bottom of the vessel and compact into a more consolidated form ("sediment").

The "adding" according to step (a) of the inventive method can be carried out by any method or measure known to a person skilled in the art as suitable for the inventive purpose.

Within the present invention the term "clay mineral" refers to any mineral which is a hydrous aluminum phyllosilicate. Clay minerals particularly suitable for the inventive method belong to the class of smectites or illites such as bentonite, montmorillonite or saponite and mixtures thereof. Other suitable clay minerals belong to the group of kaolin.

Within a particularly suitable embodiment of the present invention the term "clay mineral" refers to a natural bleaching earth. The term "natural bleaching earth" is to be understood as comprising any clay mineral which can be classified as a bentonite, attapulgite, palygorskite or sepiolite and mixtures thereof. All classes of minerals are well known to a person skilled in the art and can be identified by standard measurement of chemical composition and XRD measurements i.e. their X-ray diffractogram.

Within a particular preferred embodiment of the present invention, the clay mineral to be used in the inventive method is a Calcium bentonite.

The natural bleaching earth may be either used without any kind of further activation such as thermal, acid or alkaline activation or may have been acid or alkaline activated before adding it to the liquid composition. Acid or alkaline activation of bleaching earth is known to a person skilled in the art and may be performed with a concurrent thermal treatment. Activation of bleaching earth is for example described within EP 1893329, EP 2099561 or EP 3110543.

Within the inventive method, the clay mineral is added to the liquid composition in an amount of from 0.1 to 35 wt.-% (weight clay mineral to weight liquid composition), wherein an amount from 0.5 to 30 wt.-% such as from 0.25 to 25 wt.-% or from 0.5 to 15 wt.-% or from 0.5 to 10 wt.-% or from 0.75 to 15 wt.-% or from 0.75 to 8 wt.-% is particularly effective. Other effective amounts are from 0.5 to 7 wt.-% or from 0.5 to 5 wt.-%.

According to the inventive method the clay mineral has a BET surface of from 50 to 450 $m^2/g$. Within other suitable embodiments the BET surface is to be selected from 75 to 400 $m^2/g$, from 75 to 375 $m^2/g$, from 75 to 350 $m^2/g$, from 400 $m^2/g$, from 75 to 375 $m^2/g$, from 75 to 350 $m^2/g$, from 50 to 250 $m^2/g$, from 50 to 230 $m^2/g$ and from 50 to 225 $m^2/g$. Within particularly suitable embodiments the BET surface is to be selected from 50 to 225 $m^2/g$, from 50 to 215 $m^2/g$, from 50 to 205 $m^2/g$ and from 50 to 190 $m^2/g$. The parameter "BET surface" is well known to a person skilled in the art. It is measured according to DIN ISO 9277.

According to the inventive method, the clay mineral has a micropore volume of pores with a maximum diameter of 80 nm of from 0.01 to 0.75 ml/g, wherein a pore volume of pores with a maximum diameter of 80 nm of from 0.01 to 0.55 ml/g or from 0.05 to 0.45 ml/g or from 0.1 to 0.25 ml/g is also suitable for the inventive method. Within a particularly suitable embodiment of the present invention the clay mineral has a micropore volume of pores with a maximum diameter of 80 nm of from 0.01 to 0.45 ml/g, from 0.01 to 0.35 ml/g, from 0.01 to 0.30 ml/g and from 0.01 to 0.25 ml/g.

Within another suitable embodiment, the clay mineral has a micropore volume of pores with a maximum diameter of 25 nm of from 0.03 to 0.6 ml/g, wherein a pore volume of pores with a maximum diameter of 25 nm of from 0.04 to 0.5 ml/g or from 0.05 to 0.45 ml/g or from 0.055 to 0.40 ml/g is also suitable for the inventive method. Within a particularly suitable embodiment of the present invention the clay mineral has a micropore volume of pores with a maximum diameter of 25 nm of from 0.01 to 0.35 ml/g, from 0.01 to 0.30 ml/g, from 0.01 to 0.25 ml/g and from 0.01 to 0.20 ml/g.

Within another suitable embodiment, the clay mineral has a micropore volume of pores with a maximum diameter of 14 nm of from 0.03 to 0.6 ml/g, wherein a pore volume of pores with a maximum diameter of 14 nm of from 0.04 to 0.5 ml/g or from 0.05 to 0.45 ml/g or from 0.055 to 0.40 ml/g is also suitable for the inventive method. Within a particularly suitable embodiment of the present invention the clay mineral has a micropore volume of pores with a maximum diameter of 14 nm of from 0.01 to 0.25 ml/g, from 0.01 to 0.20 ml/g, from 0.01 to 0.15 ml/g and from 0.01 to 0.12 ml/g.

The micropore volume has been determined according to the BJH method according to DIN 66134. Pore volumes of defined ranges of pore diameter were measured by summing up incremental pore volumes, which were determined from the adsorption isotherm according BJH. Both measurements are well known to a person skilled in the art.

According to the inventive method, the clay mineral has a $SiO_2$ content of from 25 to 98 wt.-%, wherein a $SiO_2$ content of from 30 to 95 wt.-%, from 30 to 90 wt.-% or from 35 to 85 wt.-% is also suitable. Further $SiO_2$ contents of the clay mineral suitable for the inventive method are from 45 to 98 wt.-% or from 45 to 95 wt.-% or from 55 to 90 wt.-%. Within a particularly suitable embodiment of the present invention the SiO2 content is selected from the group consisting of a range of from 25 to 75 wt.-%, from 25 to 65 wt.-%, from 25 to 60 wt.-% and from 30 to 60 wt.-%. The measurement of the $SiO_2$ content of a clay mineral is well known to a person skilled in the art and exemplarily described within EP 2099561.

According to the inventive method, the clay mineral has a cation exchange capacity of from 20 to 120 mVal/100 g. Other suitable ranges of the cation exchange capacity are from 25 to 110 mVal/100 g, from 35 to 100 mVal/100 g or from 45 to 90 mVal/100 g. Further cation exchange capacities of the clay mineral of the inventive method are selected from the range of from 20 to 75 mVal/100 g or from 75 to 120 mVal/100 g. Cation-exchange capacity (CEC) is a measure of how many cations can be retained on soil particle surfaces. The measurement of the cation exchange capacity is well known to a person skilled in the art and exemplarily described in EP 1893329 which is herein incorporated by reference.

Within another suitable embodiment of the inventive method, the clay mineral has a chloride content of less than 0.1 mg Cl/g, whereas chloride contents of less than 0.75 mg Cl/g, less than 0.6 mg Cl/g, less than 0.4 mg Cl/g, less than 0.3 mg Cl/g, less than 0.2 mg Cl/g and less than 0.1 Cl/g are particularly suitable. The measurement of the chloride content is well known to a person skilled in the art and is preferably conducted by the use of nitric acid and titration with silver nitrate.

Within another suitable embodiment of the inventive method, the clay mineral has a pore size distribution with less than 15% of pores with a pore diameter of more than 150 µm, from 5 to 25% of pores with a pore diameter of more than 100 µm, from 18 to 45% of pores with a pore diameter of more than 63 µm, from 30 to 50% of pores with a diameter of more than 45 µm and from 45 to 75% of pores with a diameter of more than 25 µm. Other particularly suitable pore size distributions are less than 10% of pores with a pore diameter of more than 150 µm, from 5 to 20% of pores with a pore diameter of more than 100 µm, from 22 to 40% of pores with a pore diameter of more than 63 µm, from 35 to 45% of pores with a diameter of more than 45 µm and from 55 to 70% of pores with a diameter of more than 25 µm.

Within another suitable embodiment, the clay mineral has an $Al_2O_3$ content of from 12 to 35 wt.-%.

After adding the clay mineral to the liquid composition according to step (a) of the inventive method, the clay mineral is separated from the liquid composition after a reaction time of from 10 seconds to 90 minutes according to step (b) of the inventive method. Within a particularly suitable embodiment of the inventive method, the reaction time is selected from the range of from 30 seconds to 60 minutes, from 1 minute to 60 minutes, from 5 minutes to 60 minutes or from 15 minutes to 60 minutes. The separation can be carried out by any method known to a person skilled in the art as suitable for the inventive purpose but may be carried out by solid-liquid separation using e.g. a filter press.

Within a particularly suitable embodiment of the inventive method from 0.1 to 30 wt.-% of a filtration aid are added to the liquid composition before carrying out step (b), whereas from 0.2 to 25 wt.-%, from 0.5 to 20 wt.-% and from 1 to 15 wt.-% are also suitable. Within an even more suitable embodiment of the inventive method, the ratio of the amount of clay mineral to the amount of filtration aid is from 1:1 to 2:3.

It is thereby particularly suitable to select the amount of filtration aid within the compound mix of filtration aid and clay mineral within the range of from 50 wt.-% to 60 wt.-% and the amount of clay mineral within the compound mix of filtration aid and clay mineral within the range of from 40 wt.-% to 50 wt.-%.

Within a particularly suitable embodiment, the inventive method further contains the step (a0) subjecting the fermented medium to a solid liquid separation to obtain a supernatant Within the inventive method, step (a0) is to be carried out before step (a). The solid-liquid separation can be carried out by any method known to a person skilled in the art as suitable for the inventive purpose. A possible method is the use of a filter press.

Within another even more suitable embodiment, the inventive method further contains the step (a1) subjecting the supernatant obtained by the solid liquid separation to an ultrafiltration and wherein step (a1) is carried out after step (a0) but before step (a).

The ultrafiltration may be carried out by any method known to a person skilled in the art as suitable for the inventive purpose. A particular suitable method to carry out the ultrafiltration is a filtration method using membranes in which forces like pressure or concentration gradients lead to a separation through a semipermeable membrane. Suspended solids and solutes of high molecular weight are retained in the so-called retentate, while water and low molecular weight solutes pass through the membrane in the permeate (filtrate). An even more suitable method to carry out the ultrafiltration is a filtration method using a membrane containing or consisting of the polymer PES (poly ether sulfone) with a pore size of 10 kDa. Ultrafiltration is well known to a person skilled in the art any frequently applied to filter protein solutions such as fermented media.

In case the inventive method comprises an ultrafiltration step according to step (a1), the "liquid composition" used within the inventive method according to step (a) is the retentate obtained by the ultrafiltration according to step (a1).

Within a further aspect, the present invention relates to the use of a clay mineral with a BET surface area of from 50 to 450 m²/g, a micropore volume of pores with a maximum diameter of 80 nm of from 0.01 to 0.75 ml/g, a $SiO_2$ content of from 25 to 85 wt.-% and a cation exchange capacity of from 20 to 120 mVal/100 g for the purification of liquid compositions containing at least one sphingolipid.

The definitions and explanations given above regarding the inventive method apply also and without exception to the inventive use of the clay mineral for the purification of liquid compositions containing at least one sphingolipid.

In the following particularly preferred embodiments of the inventive method are described which are not to be understood as limiting the invention in any respect. It is to be understood that irrespective of the following particularly preferred embodiments any combination of the features as defined before is within the scope of the present invention.

Particularly Preferred Embodiment 1

Method for purification of liquid compositions containing at least one sphingolipid comprising the following steps
(a) adding from 0.1 to 35 wt.-% of a clay mineral with a BET surface area of from 75 to 400 m$^2$/g, a micropore volume of pores with a maximum diameter of 80 nm of from 0.05 to 0.45 ml/g, a SiO$_2$ content of from 45 to 98 wt.-% and a cation exchange capacity of from 35 to 100 mVal/100 g to the liquid composition;
(b) separating the clay mineral after a reaction time of from 10 seconds to 90 minutes, preferably from 1 minute to 60 minutes.

Particularly Preferred Embodiment 2

Method according to particularly preferred embodiment 1, wherein the clay mineral is a natural bentonite, preferably a Calcium bentonite.

Particularly Preferred Embodiment 3

Method according to particularly preferred embodiment 1, wherein the clay mineral is an acid or alkaline activated bentonite, preferably a Calcium bentonite.

Particularly Preferred Embodiment 4

Method according to any of particularly preferred embodiments 1 to 3, wherein the clay mineral has a chloride content of less than 0.3 mg Cl/g.

Particularly Preferred Embodiment 5

Method according to any of particularly preferred embodiments 1 to 4, wherein the clay mineral has a micropore volume of pores with a maximum diameter of 25 nm of from 0.04 to 0.5 ml/g and wherein the clay mineral has a micropore volume of pores with a maximum diameter of 14 nm of from 0.04 to 0.5 ml/g

Particularly Preferred Embodiment 6

Method according to any of particularly preferred embodiments 1 to 5, wherein liquid composition is a fermented medium, preferably a medium fermented by a filamentous fungus or a yeast, preferably with an initial (i.e. before fermentation) glucose content of from 35 to 85 wt.-% or from 40 to 65 wt.-% wherein media with an additional initial (i.e. before fermentation) content of di- and/or oligo-saccharides are particularly suitable.

Particularly Preferred Embodiment 7

Method according to particularly preferred embodiment 6, wherein the medium has been heat-treated before the fermentation is carried out, preferably at a temperature selected from the range of from 100 to 220° C. wherein from 100 to 140° C. is particularly preferred, and for a time period of from 30 minutes to 12 hours or from 1 hour to 10 hours.

Particularly Preferred Embodiment 8

Method according to any of particularly preferred embodiments 1 to 7, wherein clay mineral is added in an amount of from 0.1 to 15 wt.-% (weight clay mineral to weight liquid composition), wherein the ratio of the amount of clay mineral to the amount of filtration aid is preferably from 1:1 to 2:3.

Particularly Preferred Embodiment 9

Method according to particularly preferred embodiment 8, wherein the amount of filtration aid is selected within the compound mix of filtration aid and clay mineral within the range of from 50 to 60 wt.-% (weight filtration aid to weight liquid composition) and the amount of clay mineral within the compound mix of filtration aid and clay mineral is selected within the range of from 40 wt.-% to 50 wt.-%.

Particularly Preferred Embodiment 10

Method according to any of particularly preferred embodiments 1 to 9, wherein the method further contains the steps
(a0) subjecting the fermented medium to a solid liquid separation to obtain a supernatant, wherein step (a0) is to be carried out before step (a) and wherein the solid liquid separation is carried out by use of a filter press to obtain a supernatant and
(a1) subjecting the supernatant obtained by the solid liquid separation according to step (a0) to an ultrafiltration and wherein step (a1) is carried out after step (a0) but before step (a).

Particularly Preferred Embodiment 11

Method according to any of particularly preferred embodiments 1 to 10, wherein the clay mineral has a pore size distribution with less than 10% of pores with a pore diameter of more than 150 µm, from 5 to 15% of pores with a pore diameter of more than 100 µm, from 18 to 40% of pores with a pore diameter of more than 63 µm, from 30 to 40% of pores with a diameter of more than 45 µm and from 45 to 65% of pores with a diameter of more than 25 µm.

Particularly Preferred Embodiment 12

Use of a clay mineral with a BET surface area of from 75 to 400 m$^2$/g, a micropore volume of pores with a maximum diameter of 80 nm of from 0.05 to 0.45 ml/g, a SiO$_2$ content of from 45 to 98 wt.-% and a cation exchange capacity of from 35 to 100 mVal/100 g to the liquid composition for the purification of liquid compositions containing at least one sphingolipid.

Particularly Preferred Embodiment 13

Use according to particularly preferred embodiment 12, wherein the clay mineral is a natural bentonite, preferably a Calcium bentonite.

Particularly Preferred Embodiment 14

Use according to any of particularly preferred embodiments 12 or 13, wherein the clay mineral is an acid or alkaline activated bentonite, preferably a Calcium bentonite.

Particularly Preferred Embodiment 15

Use according to any of particularly preferred embodiments 12 to 14, wherein the clay mineral has a chloride content of less than 0.3 mg Cl/g.

Particularly Preferred Embodiment 16

Use according to any of particularly preferred embodiments 12 to 15, wherein liquid composition is a fermented medium, preferably a medium fermented by a filamentous fungus or a yeast.

Particularly Preferred Embodiment 17

Use according to particularly preferred embodiment 16, wherein the medium has been heat-treated before the fermentation is carried out, preferably at a temperature selected from the range of from 100 to 220° C. wherein from 100 to 140° C. is particularly preferred.

Particularly Preferred Embodiment 18

Method for purification of liquid compositions containing at least one sphingolipid comprising the following steps (a) adding from 0.1 to 35 wt.-% of a clay mineral with a BET surface area of from 50 to 210 m$^2$/g, a micropore volume of pores with a maximum diameter of 80 nm of from 0.01 to 0.25 ml/g, a SiO2 content of from 25 to 60 wt.-% and a cation exchange capacity of from 35 to 100 mVal/100 g to the liquid composition;

(b) separating the clay mineral after a reaction time of from 10 seconds to 90 minutes, preferably from 1 minute to 60 minutes.

Particularly Preferred Embodiment 19

Method for purification of liquid compositions containing at least one sphingolipid comprising the following steps (a) adding from 0.1 to 35 wt.-% of a clay mineral with a BET surface area of from 50 to 180 m$^2$/g, a cation exchange capacity of from 42 to 110 mVal/100 g and a quantity of particles with a particle size of at least 63 μm of less than 15% to the liquid composition;

(b) separating the clay mineral after a reaction time of from 10 seconds to 90 minutes, preferably from 1 minute to 60 minutes.

Particularly Preferred Embodiment 20

Use of a clay mineral with a BET surface area of from 50 to 180 m$^2$/g, a cation exchange capacity of from 42 to 110 mVal/100 g and a quantity of particles with a particle size of at least 63 μm of less than 15% for the purification of liquid compositions containing at least one sphingolipid and at least one enzyme.

EXAMPLES

The present invention is now described by the following examples and figures. The examples and figures are for illustrative purposes only and are not to be understood as limiting the invention.

Example 1—Choice of Adsorbent

A supernatant originating from fermentation by a *Trichoderma reesei* RutC30 strain was treated with several adsorbents in order to remove sphingolipids from the supernatant. If this substance stayed in the solution, it would cause a rise in turbidity and finally a layer of sediment if the supernatant was stored at temperature above 21° C. which would usually afford cooling during storage.

The following adsorbents were tested.

| Tube Nr. | Category | Characteristics | |
|---|---|---|---|
| 1 | Anion exchanger | Matrix: Crosslinked acrylic gel structure | |
| | | Functional Group: Tertiary amine | |
| 2 | Cation exchanger | Matrix: Styrene divinylbenzene copolymer | |
| | | Functional Group: Sulfonic acid | |
| 3 | Clay Mineral I | Type: Thermal activated Calcium Bentonite | |
| | | BET surface area: | 60 m$^2$/g |
| | | Micropore volume of pores: | |
| | | 0-80 nm | 0.09 ml/g |
| | | 0-25 nm | 0.07 ml/g |
| | | 0-14 nm | 0.06 ml/g |
| | | SiO$_2$ content: | 58% |
| | | cation exchange capacity: 51 mVal/100 g | |
| | | Particle size: | |
| | | >150 μm | 1% |
| | | >100 μm | 9% |
| | | >63 μm | 25% |
| | | >45 μm | 42% |
| | | >25 μm | 63% |
| 4 | Clay Mineral II | Type: Sour activated Calcium Bentonite | |
| | | BET surface area: | 300 m$^2$/g |
| | | Micropore volume of pores: | |
| | | 0-80 nm | 0.43 ml/g |
| | | 0-25 nm | 0.37 ml/g |
| | | 0-14 nm | 0.34 ml/g |
| | | SiO$_2$ content: | 69.3% |
| | | cation exchange capacity: 30 mVal/100 g | |
| | | Particle size: | |
| | | >150 μm | 9% |
| | | >100 μm | 17% |
| | | >63 μm | 31% |
| | | >45 μm | 41% |
| | | >25 μm | 59% |
| 5 | Blank | — | |

The supernatant was distributed on five 5 ml tubes. Every tube was filled with 4 g supernatant. 0.4 g of the adsorbents named above were added to the respective tube. The blanc remained untreated. The mixtures were incubated at room temperature in an overhead shaker for 30 min. After the incubation, the tubes were centrifuged to separate the adsorbents from the solution. The supernatants were poured into 5 new 5 ml tubes. The supernatants were incubated for 10 days at 25° C. and after that centrifuged for 5 minutes at 12.700 rpm. As expected in tube 5, the blanc, the sediment occurred, and a pellet built up after centrifugation. The same happened for tube 1 and 2. The supernatants stored in tube 3 and 4 stayed clear and did not show a pellet. The weight of the wet pellets is shown in FIG. 1. This example shows that both bentonite adsorbents (Clay Mineral I and II) can remove the sediment-causing substance. All following examples were performed with the bentonite Clay Mineral I (Tube Nr. 3).

Example 2—Determination of Dosage Minimum

A supernatant originating from fermentation by a *Trichoderma reesei* RutC30 was treated with several amounts of the bentonite Clay Mineral I to obtain the minimal effective dosage quantity, ranging from 0.01 wt.-% to 2 wt.-%. The supernatant was distributed on seven 50 ml tubes. Every tube was filled with 30 g supernatant. The following amounts of Clay Mineral I were added.

| Tube Nr. | Amount of Clay Mineral I [wt.-%] |
| --- | --- |
| 1 | 0.00 |
| 2 | 0.01 |
| 3 | 0.05 |
| 4 | 0.10 |
| 5 | 0.50 |
| 6 | 1.00 |
| 7 | 2.00 |

The mixtures were incubated at room temperature in an overhead shaker for 60 min. After that, Clay Mineral I was removed by filtration (cutoff of 0.2 μm). The filtrates were put into new 50 ml tubes and incubated at 25° C. The turbidity of these filtrates was measured right after the filtration, on day 6, day 9, day 13, day 23, day 48 and on day 90 after the adsorption. It was measured in FNU (Formazine Nephelometric Units). The results can be found in figure Nr. 2. It can be seen that if the supernatant is not treated with Clay Mineral I (0.00 wt.-%), the turbidity triples over a period of only 3 months. The formation of turbidity can be halved with a treatment of 0.5 wt.-% and nearly fully avoided by the addition of 2.00 wt.-%. As a conclusion, the treatment with 0.5 wt.-% of Clay Mineral I was determined as the dosage minimum.

Example 3—Determination of Ideal Incubation Time

To obtain the ideal incubation time, a supernatant originating from fermentation by a *Trichoderma reesei* RutC30 strain was distributed on four 50 ml tubes, every tube was filled with 30 g of supernatant. Three of them were treated with 0.5 wt.-% of Clay Mineral I and incubated according to the table below. Additionally, one blanc was taken along for comparison. The blanc did not experience any Clay Mineral I treatment.

| Tube Nr. | Incubation time |
| --- | --- |
| 1 | 1 |
| 2 | 3 |
| 3 | 19 |
| 4 | Blanc (no treatment with Clay Mineral I) |

The mixtures were incubated at room temperature in an overhead shaker. After that Clay Mineral I was removed by filtration (cutoff of 0.2 μm). The filtrates were put into new 50 ml tubes and incubated at 25° C. The turbidity of these filtrates was measured right after the filtration, on day 6, day 9, day 13, day 23, day 48 and on day 90 after the adsorption. It was measured in FNU (Formazine Nephelometric Units). The results can be found in figure nr. 3. The diagram reveals, that one hour of incubation gives the same long-term-effect as 19 hours of incubation. The turbidity is reduced to the same level.

Example 4—Integration into an Industrially Applicable Process

In order to integrate the Clay Mineral I treatment in an industrially applicable downstream process, any clay mineral used within the inventive process needs to be removable by a filtration step that can withdraw a large quantity of solids. Pretests for the filter press were done by a pressure nutsche. This device resembles the conditions on a filter press which is widely used within processes on industrial scale. For an advanced particle removal, as a standard, 5 wt.-% of a filtration aid were added to the supernatant before running through the nutsche.

A filter aid with the following parameters was used:

| Parameter | Specification |
| --- | --- |
| Type | Perlite, Amorphous Silicate |
| Physical Form | Dry powder |
| Flowrate (PFRv) | 16-40 |
| Cake density (wet) | max. 26.0 lbs/ft$^3$ |
| Float | max. 2 (ml/20 g) |

In this experiment, the amount of filtration aid was gradually replaced by Clay Mineral I. The supernatant was distributed on six 200 ml beakers, every beaker was filled with 100 g of supernatant. The content was treated with filtration aid and Clay Mineral I, following the table below, and incubated for one hour at 21° C.

| Tube Nr. | Filter Aid [wt.-%] | Clay Mineral I [wt.-%] |
| --- | --- | --- |
| 1 | 0 | 5 |
| 2 | 1 | 4 |
| 3 | 2.5 | 2.5 |
| 4 | 3 | 2 |
| 5 | 4 | 1 |
| 6 | 5 | 0 |

Figure 4:
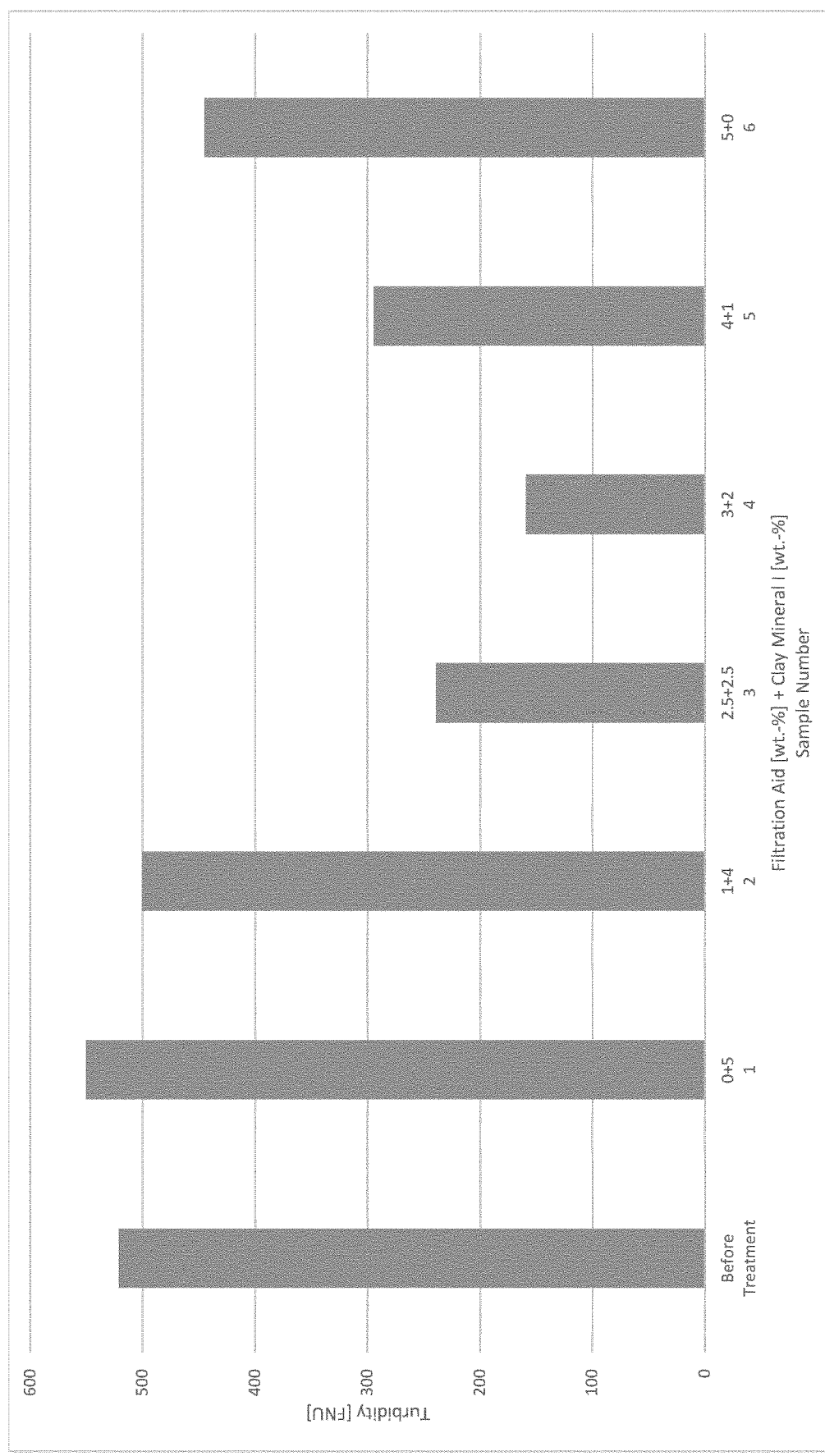
FIG. 4: shows the turbidities of a supernatant originating from fermentation by a *Trichoderma reesei* RutC30, after different treatments. The first one remained without treatment. The following five columns show the turbidity after the treatment with varying combinations of filtration aid and Clay Mineral I. This figure illustrates example 4.

A run on the pressure nutsche was performed for every of the six samples. The samples were pressed though the filter cloth with a N2 pressure of 200 mbar. A filter cloth with the tradename PPD3133 (500 L/dm$^2$/min) was used. FIG. 4 shows the turbidities of the filtrates after filtration. The lower the turbidity, the more successful was the filtration. An important parameter for estimating the filtering quality is the creation of a fine filter cake. For sample Nr. 1, no filter cake built up. This means, Clay Mineral I could not be held back by the filter cloth and was found in the filtrate. This fact explains the rise in turbidity of filtrate 1, compared to the untreated material. The mixture of 3 wt.-% filtration aid and 2 wt.-% Clay Mineral I created a jelly-like filter cake. It means, that the filtration aid is able to hold Clay Mineral I back, in this combination. This was validated also by the low filtrate turbidity of sample 4. The sample treated with 5 wt.-% filtration aid built up a powdery filter cake. This cake cannot reduce the start turbidity as much as the combination in sample 4. This means, that Clay Mineral I has—in addition to its excellent adsorber—quality, also a filtering effect when mixed with the filtration aid.

Example 5—Identification of Sediment Causing Substance

This example consists of 2 experiments.

The first one was the analysis of the sediment. The second one the analysis of the particles bound by the Clay Mineral I powder after the treatment.

For experiment 1 a supernatant originating from fermentation by a *Trichoderma reesei* RutC30 strain was distributed on three 5 ml tubes. Every tube was filled with 4 g of supernatant and incubated at 25° C. Sediment was built up after 10 days.

The tubes were centrifuged. Pellet 1 was mixed with an 80% methanol solution, pellet 2 with isopropanol and pellet 3 with hexane to resolve the precipitated substances. The tubes were centrifuged again to separate the solvents from the insoluble fraction of the pellets.

All solvents containing the resolved substances were analyzed in a LC-MS measurement. LC-MS analysis was performed using an Ultimate 3000 UPLC system (Thermo Fisher Scientific, Germany) coupled to a Q-Exactive Plus mass spectrometer (Thermo Fisher Scientific, Germany) equipped with a HESI-II ion source.

Separation was achieved with a Nucleodur C18 Gravity column (100×2 mm, i.d. 1.8 μm) using 0.1% formic acid in water (solvent A) and 0.1% formic acid in acetonitrile (solvent B) as mobile phases. The flow rate was 0.25 mL/min and the column oven was kept at 35° C.

The gradient used for separation was as follows: 0 min, 0% B; 3 min, 0% B; 15 min, 95% B; 17 min, 95% B; 18 min, 0% B; 22 min, 0% B.

The Q Exactive Plus was run in the positive ionization mode. The ion source temperature was set to 400° C. and the spray voltage was 3500 V. A full-scan/dd-MS$^2$ Top 5 MS method was used for sample analysis. The resolution of the full-scan was set to 70 000 and ions were detected within a scan range of 100-1000 m/z. The Top 5 ions were isolated (isolation window: 1.6 m/z) and fragmented via HCD with an energy of 20 eV.

Neither the isopropanol nor the hexane sample showed peaks in the LC-MS diagram.

Figure 5:
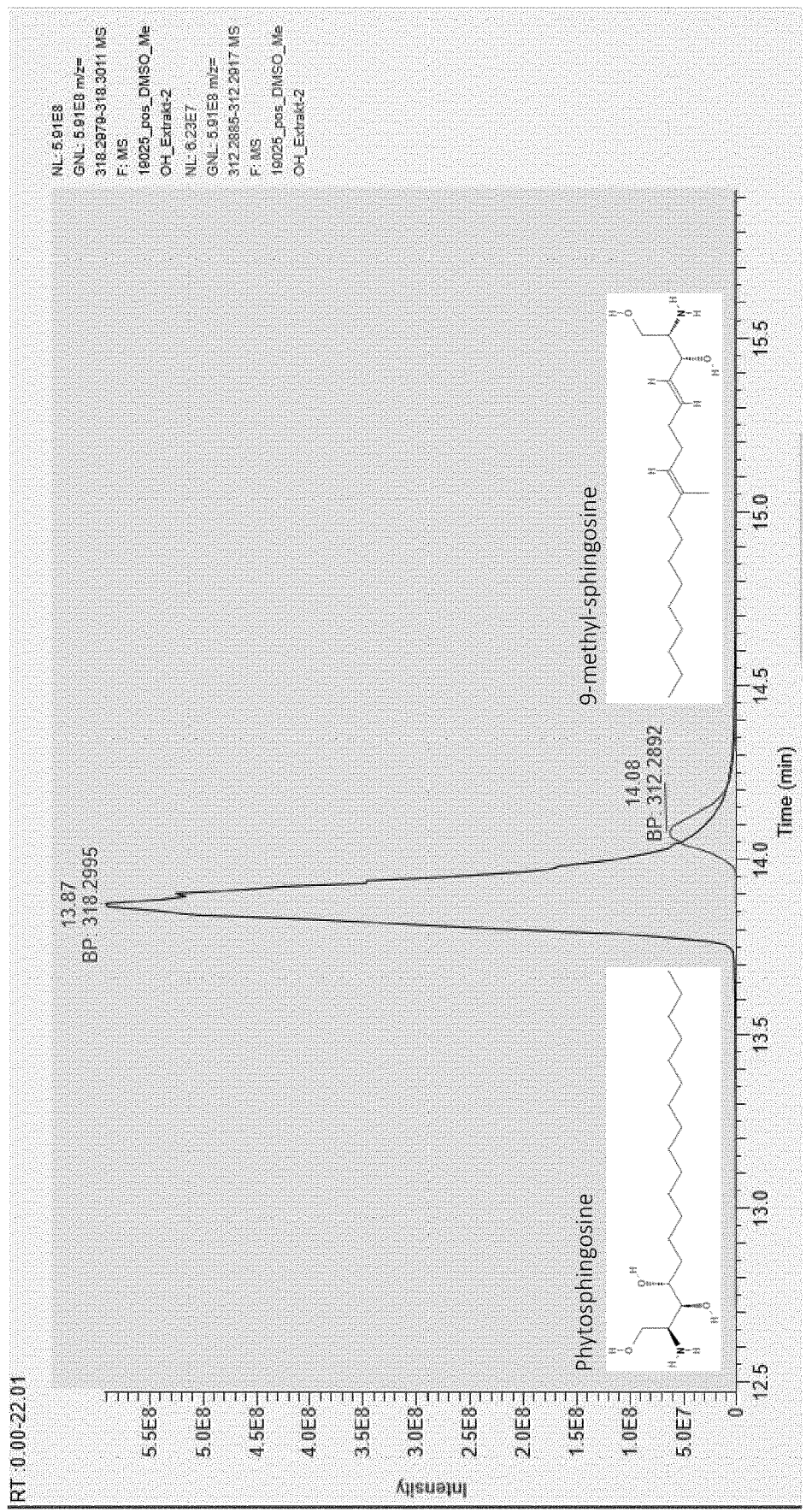
FIG. 5: shows an extracted ion chromatogram with phytophingosine and 9-methyl-sphingosine. This figure illustrates example 5, experiment 1.

The 80% methanol sample in contrast showed a change in color and revealed in the LC-MS analysis amongst others two dominant peaks. An extracted ion chromatogram showing these peaks is depicted in FIG. 5. The detected masses were m/z [M+H]+=318.2991 (Δm=3.6 ppm; sum formula: C18H39NO3) at a retention time of 13.87 min and m/z [M+H]+=312.2892 (Δm=1.6; sum formula: C19H37NO2) at a retention time of 14.08 min. Their sum formula as well as their MS/MS fragmentation pattern match those of phytosphingosine and 9-methyl-sphingosine. Other peaks can be determined as a mix of fatty acids and sphingolipid derivatives.

This proves that the sediment contained a considerable amount of phytosphingosine and 9-methyl-sphingosine in the supernatant which caused the observed turbidity.

The second experiment dealt with the following question: Are these substances taken out of the supernatant during the inventive method?

To answer the question, 5 ml of fresh supernatant was treated with 2 wt.-% of Clay Mineral I and incubated for one hour. The Clay Mineral I was removed by centrifugation for 5 minutes at 12.700 rpm. The Clay Mineral I pellet was mixed with 4 ml of pure methanol. After an incubation time of 1 hour, this mix was centrifuged again for 5 minutes at 12.700 rpm. The supernatant methanol was then analyzed in a LC-MS measurement under the same conditions as in experiment 1.

Figure 6:
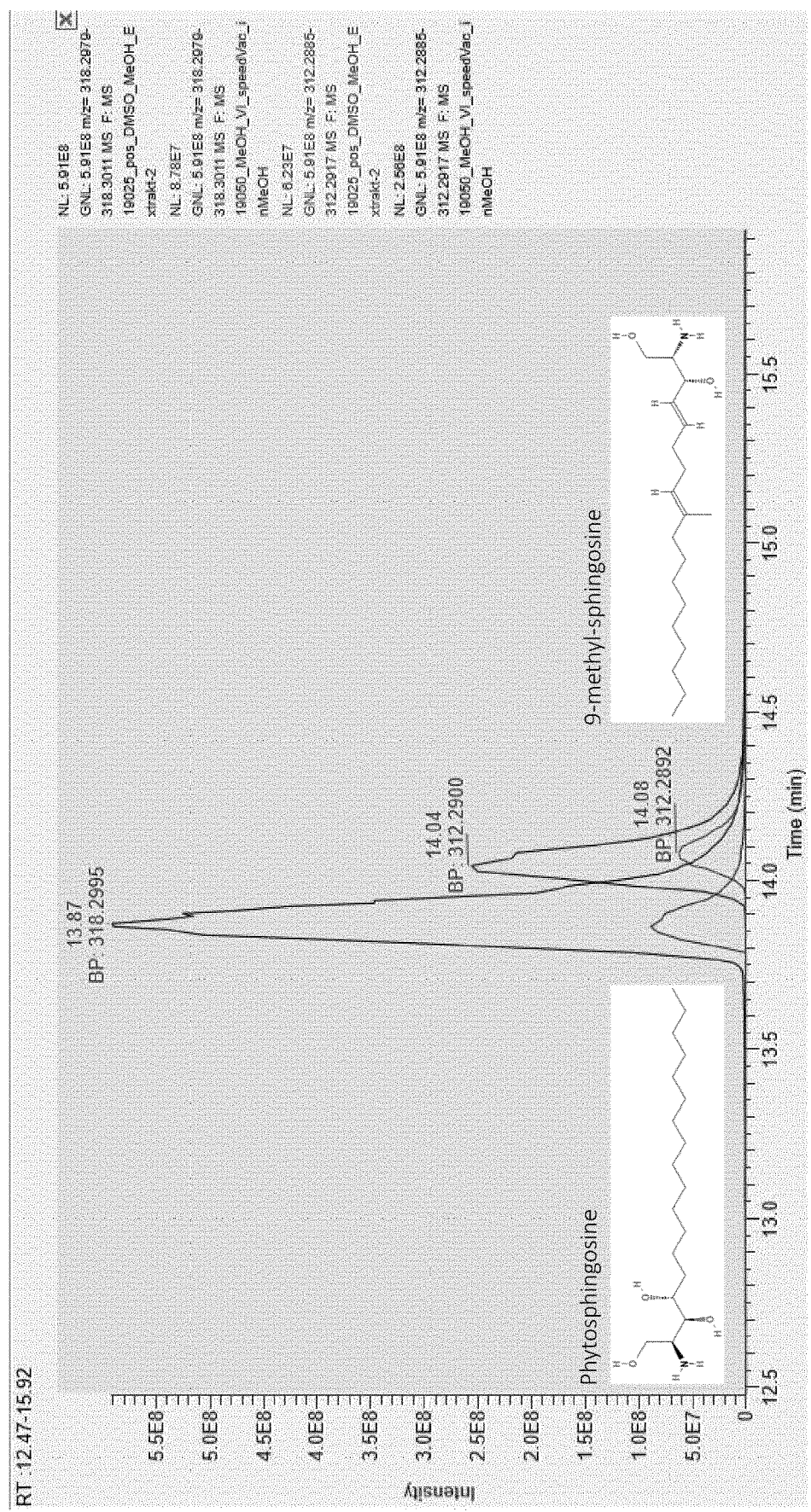
FIG. 6: shows another extracted ion chromatogram. It is an overlay of the peaks, found in the precipitate analysis and the peaks found in the pellet analysis of Clay mineral I. This figure illustrates example 5, experiment 2.

The analysis revealed, that also the two peaks at a retention time of 13.87 min and 14.08 min were dominant. FIG. 6 shows another extracted ion chromatogram with an overlay of the peaks, found in the precipitate analysis and the peaks found in pellet analysis of Clay mineral I. For this reason, it can be stated, that phytosphingosine and 9-methyl-sphingosine adsorbed to the Clay mineral I powder during the treatment and can hence be taken out of the product by the inventive method. With these sphingolipids taken out of the product, the stability is raised and precipitation at 25° C. can be prevented.

Example 6—Determination of Stability

A supernatant originating from fermentation by a *Trichoderma reesei* RutC30 strain (in the following "supernatant") was treated with several clay minerals in order to remove sphingolipids from the supernatant.

The following clay minerals were tested.

| Tube Nr. | Category | Characteristics | | |
|---|---|---|---|---|
| 1 | Clay Mineral III | Type: Mixture of bentonite and amorphous silica | | |
| | | BET surface area: | | 220 m$^2$/g |
| | | cation exchange capacity: 40 mVal/100 g | | |
| | | Particle size: | | |
| | | | >150 μm | 7% |
| | | | >100 μm | 18% |
| | | | >63 μm | 33% |
| | | | >45 μm | 42% |
| | | | >25 μm | 53% |
| 2 | Clay Mineral IV | Type: Acid activated bleaching earth | | |
| | | BET surface area: | | 200 m$^2$/g |
| | | cation exchange capacity: 28 mVal/100 g | | |
| | | Particle size: | | |
| | | | >150 μm | 7% |
| | | | >100 μm | 14% |
| | | | >63 μm | 30% |
| | | | >45 μm | 43% |
| | | | >25 μm | 64% |

-continued

| Tube Nr. | Category | Characteristics | |
|---|---|---|---|
| 3 | Clay Mineral V | Type: Natural calcium sodium bentonite (montmorillonite) BET surface area: cation exchange capacity: 71 mVal/100 g Particle size: | 0.88 m²/g |
| | | >150 µm | 3% |
| | | >100 µm | 10% |
| | | >63 µm | 24% |
| | | >45 µm | 37% |
| | | >25 µm | 52% |
| 4 | Clay Mineral VI | Type: Alkaline activated bentonite (montmorillonite) BET surface area: cation exchange capacity: 78 mVal/100 g Particle size: | 27 m²/g |
| | | >150 µm | 0% |
| | | >100 µm | 0% |
| | | >63 µm | 2% |
| | | >45 µm | 12% |
| | | >25 µm | 35.% |
| 5 | Clay Mineral VII | Type: Alkaline activated bentonite (montmorillonite) BET surface area: cation exchange capacity: 93 mVal/100 g Particle size: | 79.96 m²/g |
| | | >150 µm | 0% |
| | | >100 µm | 0% |
| | | >63 µm | 0% |
| | | >45 µm | 1% |
| | | >25 µm | 6% |
| 6 | Clay Mineral VIII | Type: Alkaline activated bentonite (montmorillonite) BET surface area: cation exchange capacity: 73 mVal/100 g Particle size: | 1.76 m²/g |
| | | >150 µm | 0% |
| | | >100 µm | 0% |
| | | >63 µm | 0.% |
| | | >45 µm | 0.5% |
| | | >25 µm | 8.4% |
| 7 | Clay Mineral I | Type: Thermal activated Calcium Bentonite BET surface area: cation exchange capacity: 51 mVal/100 g Particle size: | 60 m²/g |
| | | >150 µm | 1% |
| | | >100 µm | 9% |
| | | >63 µm | 25% |
| | | >45 µm | 42% |
| | | >25 µm | 63% |
| 8 | Blank | | |

Figure 7:
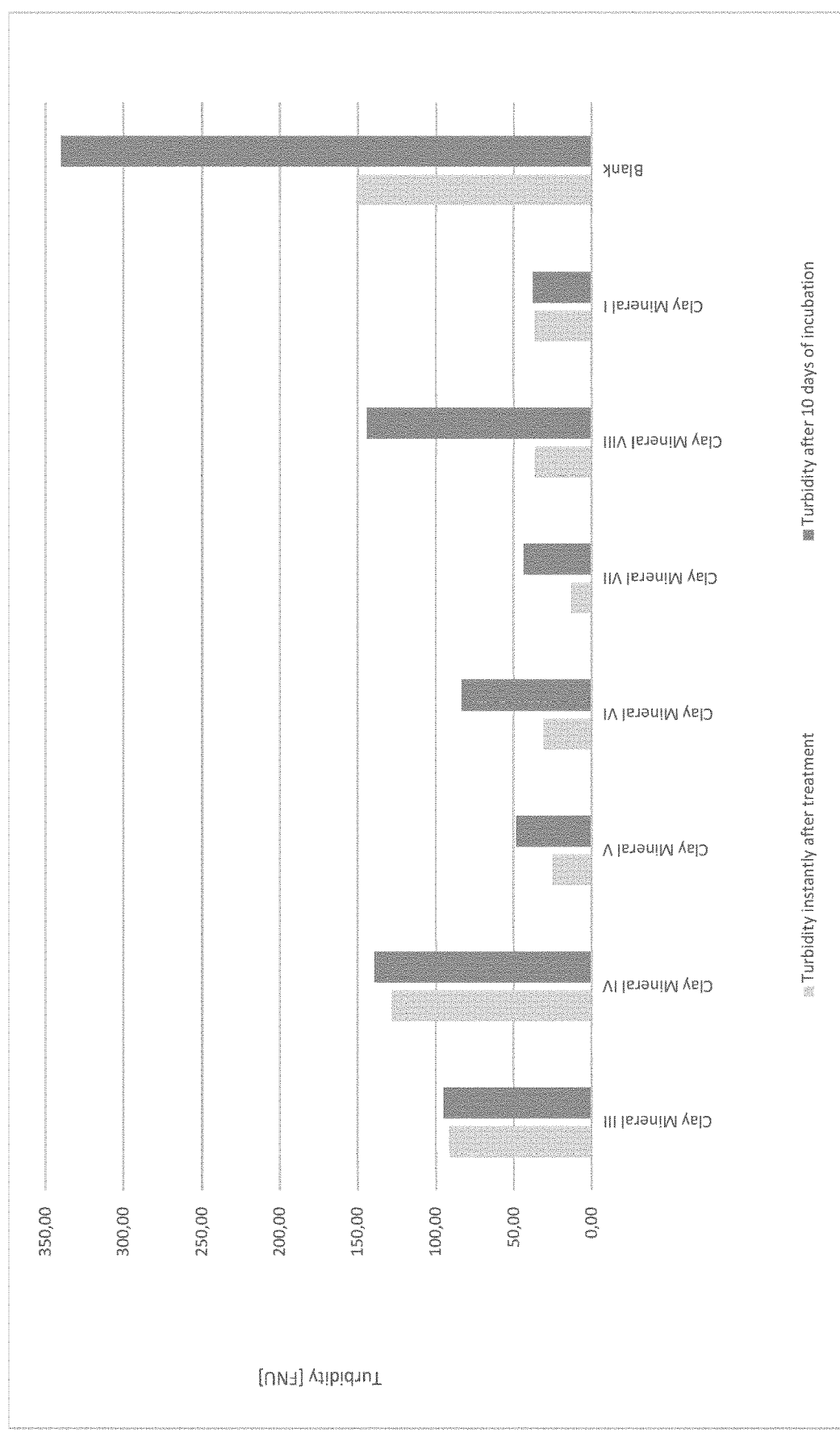
FIG. 7: shows turbidity after clay mineral treatment including turbidity after 10 days of storage time.

The supernatant was distributed on eight 50 ml tubes. Every tube was filled with 20 g supernatant. 2 g of each clay mineral sample (Clay Minerals I, III, IV, V, VI, VII and VIII) were added to the respective tube. The blanc remained untreated. The mixtures were incubated at room temperature in an overhead shaker for 30 min. After the incubation, the tubes were centrifuged to separate the clay mineral samples from the solution. The supernatants were poured into eight new 50 ml tubes. Turbidity was measured instantly. The supernatants were incubated for 10 days at 25° C. and after that turbidities were measured again. As expected in tube 8 (blanc) sediment formation occurred. It could be shown that clay minerals with a BET surface from 60 to 180 m²/g, a cation exchange capacity of from 42 to 110 mVal/100 g and a low quantity of particles with a particle size of at least 63 µm show not only reduced turbidity right after treatment but show low turbidity even after 10 days of storage time. The results of example 6 are illustrated in FIG. 7.

Example 7—Enzyme Activity and Long-Term Stability of Supernatant after Treatment with Clay Mineral I 120 ml of a supernatant, originating from fermentation by a *Trichoderma reesei* RutC30 (in the following "supernatant"), served as material for this example. 60 ml were treated with 0.5 wt.-% Clay Mineral I. After the treatment, this supernatant was distributed onto three 50 ml tubes in order to perform a stability test, 20 ml in every tube. The three Tubes were stored at 3 temperatures, 5° C., 25° C. and 40° C. in order to perform a long-term stability test. As a blank, the remaining 60 ml of supernatant were distributed also onto three 50 ml tubes and stored at 5° C., 25° C. and 40° C. As the supernatant contains active enzymes, the enzyme activity served as a parameter to measure the stability of the supernatant. At the beginning, after 5 weeks, after 26 weeks and after 61 weeks, the enzyme activity was measured. The measurement was carried out as follows:

One 50 ml tube was taken out of its storage position at the respective temperature. 1 ml was taken out of the tube. The tube was put back instantly onto its storage position. The 1 ml was used to perform the activity analysis.

The sample volume was filtered through a filter with a pore size of 0.45 µm. The sample was diluted by 1:100 with the following buffer: 50 mM sodium acetate (pH 5)+0.1% Tween 20. 20 µl of the diluted sample were heated to a temperature of 37° C. 100 µl of 2 mM 4-nitrophenyl β-D-lactopyranoside, also preheated to 37° C., were added.

After an incubation time of 300 seconds, 120 µl of 1M sodium carbonate (Na2CO3), also preheated to 37° C., were added in order to lift the pH to the alkaline range. The enzymes in the solution cut 4-nitrophenol from the substrate 4-nitrophenyl β-D-lactopyranoside. At an alkaline pH, 4-nitrophenol has a yellow color. After another incubation time of 30 seconds, the yellow color of the solution is measured photometrically at 405 nm. The more active the enzymes are the stronger the yellow color. Next to the sample, a control sample is also measured within the assay. It has a defined enzyme activity, given in U/ml. By correlating the intensity of the yellow color of the control to the yellow color of the samples, also the activity in U/ml can be correlated. The output of the assay is the enzyme activity of the enzymes in the sample given in U/ml.

Figure 8:
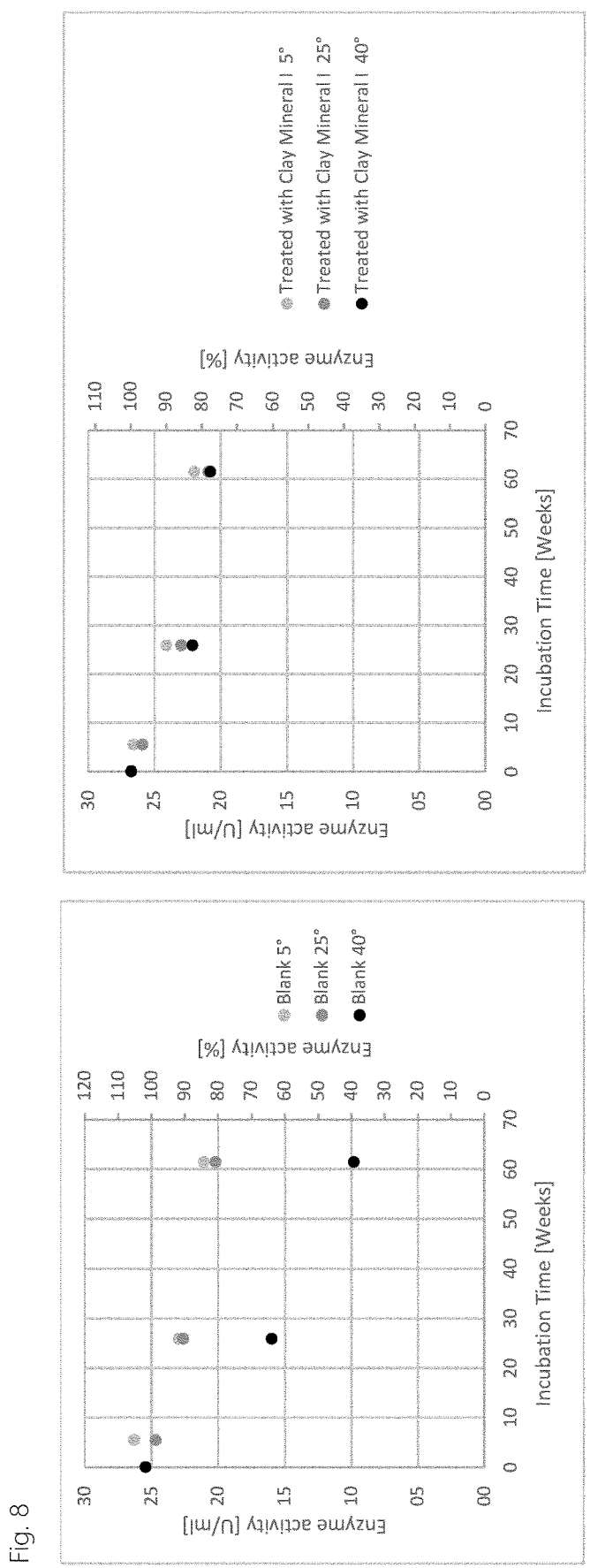
FIG. 8: shows turbidity and enzymatic activity after treatment with clay mineral 1 and long time storage conditions.

FIG. 8 shows the results of enzyme activity measurement. It can be seen, that the supernatant without Clay Mineral I treatment (Blank) has a remaining activity of 40%, after 61 weeks of incubation at 40° C. Supernatant treated with Clay Mineral I shows a remaining activity of 80% (equal storage time and temperature). Therefore, treatment with Clay Mineral I results in a higher long-term stability at elevated temperatures.

The invention claimed is:

1. A method for purification of liquid compositions containing at least one sphingolipid comprising the following steps:
    (a) adding from 0.1 to 35 wt.-% of a clay mineral with a BET surface area of from 50 to 450 m$^2$/g, a micropore volume of pores with a maximum diameter of 80 nm of from 0.01 to 0.75 ml/g, a SiO$_2$ content of from 25 to 98 wt.-% and a cation exchange capacity of from 20 to 120 mVal/100 g to the liquid composition; and
    (b) separating the clay mineral after a reaction time of from 10 seconds to 90 minutes.

2. Method according to claim 1, wherein the clay mineral has a chloride content of less than 0.1 mg Cl/g.

3. Method according to claim 1, wherein the clay mineral has a pore size distribution with less than 15% of pores with a pore diameter of more than 150 µm, from 5 to 25% of pores with a pore diameter of more than 100 µm, from 18 to 45% of pores with a pore diameter of more than 63 µm, from 30 to 50% of pores with a diameter of more than 45 µm and from 45 to 75% of pores with a diameter of more than 25 µm.

4. Method according to claim 1, wherein the clay mineral is a natural bleaching earth.

5. Method according to claim 4, wherein the natural bleaching earth is selected from the group consisting of bentonite, attapulgite, sepiolite, palygorskite or mixtures thereof.

6. Method according to claim 4, wherein the natural bleaching earth is calcium bentonite.

7. Method according to claim 4, wherein the bleaching earth is neither alkaline or acid activated.

8. Method according to claim 4, wherein the bleaching earth is acid or alkaline activated.

9. Method according to claim 1, wherein the liquid composition is a fermented medium.

10. Method according to claim 9, further containing the step
    (a0) subjecting the fermented medium to a solid liquid separation to obtain a supernatant and wherein step (a0) is carried out before step (a).

11. Method according to claim 10, further comprising the step
    (a1) subjecting the supernatant of claim 10 to an ultrafiltration and wherein step (a1) is carried out after step (a0) but before step (a).

12. Method according to claim 9, wherein the fermented medium is a medium fermented by a filamentous fungus.

13. Method according to claim 12, wherein the filamentous fungus is selected from the group consisting of *Acremonium, Aspergillus, Fusarium, Humicola, Mucor, Myceliophthora, Neurospora, Penicillium, Scytalidium, Thielavia, Tolypocladium* and *Trichoderma*.

14. Method according to claim 1 wherein from 0.1 to 30 wt.-% of a filtration aid are added to the liquid composition before carrying out step (b).

* * * * *